US012201932B2

(12) United States Patent
Skelton

(10) Patent No.: US 12,201,932 B2
(45) Date of Patent: Jan. 21, 2025

(54) AIR PURIFICATION SYSTEM FOR PASSENGER TRANSPORT CABIN

(71) Applicant: Adam R. Skelton, Murfreesboro, TN (US)

(72) Inventor: Adam R. Skelton, Murfreesboro, TN (US)

(*) Notice: Subject to any disclaimer, the term of this patent is extended or adjusted under 35 U.S.C. 154(b) by 722 days.

(21) Appl. No.: 17/501,097

(22) Filed: Oct. 14, 2021

(65) Prior Publication Data

US 2022/0118389 A1 Apr. 21, 2022

Related U.S. Application Data

(60) Provisional application No. 63/092,902, filed on Oct. 16, 2020.

(51) Int. Cl.
*B01D 46/00* (2022.01)
*A61L 9/20* (2006.01)
(Continued)

(52) U.S. Cl.
CPC .......... *B01D 46/0028* (2013.01); *A61L 9/205* (2013.01); *B01D 46/0038* (2013.01);
(Continued)

(58) Field of Classification Search
CPC ..... A61L 9/00; A61L 9/16; A61L 9/18; A61L 9/20; A61L 9/205; A61L 2209/00; A61L 2209/10; A61L 2209/11; A61L 2209/111; A61L 2209/12; A61L 2209/13; A61L 2209/134; A61L 2209/14; A61L 2209/16; B01D 46/00; B01D 46/0027; B01D 46/0028; B01D 46/0038; B01D 46/0039; B01D 46/0047; B01D 46/0049; B01D 46/56; B01D 46/58; B01D 53/00;
(Continued)

(56) References Cited

U.S. PATENT DOCUMENTS 4,804,392 A 2/1989 Spengler
5,221,520 A 6/1993 Cornwell
(Continued)

OTHER PUBLICATIONS

International Search Report and Written Opinion of related PCT application No. PCT/US21/55407; Issued Jan. 18, 2022; 8 pages.
(Continued)

*Primary Examiner* — Natasha E Young
(74) *Attorney, Agent, or Firm* — Peter L. Brewer; Thrive IP

(57) ABSTRACT

An air purification system for a passenger cabin of a transport vessel. The air purification system comprises an elongated air compartment having a panel, with a plurality of openings along the panel. Air filters reside within the openings to receive air from inside the cabin. The system also includes a plurality of air tubes. Air moves through the air tubes, aided by a source of compressed air, to motive flow valves. The motive flow valves create suction to draw air into the air compartment from the passenger cabin. The system also includes at least one UV-C light source. The UV-C light source resides within the air compartment, and disinfects the air moving through the air compartment. A plurality of air outlets are also placed along the panel, with each outlet configured to release air at selected points to provide a distribution of disinfected air into the passenger cabin.

35 Claims, 10 Drawing Sheets

(51) Int. Cl.
  *B01D 46/58* (2022.01)
  *B01D 53/00* (2006.01)
  *B60H 3/06* (2006.01)
  *B61D 27/00* (2006.01)
  *B64D 13/06* (2006.01)

(52) U.S. Cl.
  CPC ......... *B01D 46/0049* (2013.01); *B01D 46/58* (2022.01); *B01D 53/007* (2013.01); *B61D 27/0018* (2013.01); *B64D 13/06* (2013.01); *A61L 2209/111* (2013.01); *A61L 2209/12* (2013.01); *A61L 2209/14* (2013.01); *B01D 2255/802* (2013.01); *B01D 2257/708* (2013.01); *B01D 2257/90* (2013.01); *B01D 2257/91* (2013.01); *B01D 2273/30* (2013.01); *B01D 2279/65* (2013.01); *B60H 3/0608* (2013.01); *B64D 2013/0651* (2013.01)

(58) Field of Classification Search
  CPC .............. B01D 53/007; B01D 2255/00; B01D 2255/80; B01D 2255/802; B01D 2257/00; B01D 2257/70; B01D 2257/708; B01D 2257/90; B01D 2257/91; B01D 2258/00; B01D 2258/06; B01D 2259/00; B01D 2259/45; B01D 2259/4566; B01D 2259/4575; B01D 2259/804; B01D 2273/00; B01D 2273/30; B01D 2279/00; B01D 2279/65; B64D 13/00; B64D 13/06; B64D 2013/0603; B64D 2013/0625; B64D 2013/0651; B64D 2013/0688
  See application file for complete search history.

(56) References Cited

U.S. PATENT DOCUMENTS

| | | | |
|---|---|---|---|
| 5,884,873 A * | 3/1999 | Breit | B64C 21/06 244/209 |
| 8,936,671 B2 * | 1/2015 | Horstman | B64D 13/06 422/4 |
| 9,310,088 B2 | 4/2016 | Melikov et al. | |
| 9,540,252 B1 | 1/2017 | Collins et al. | |
| 9,981,056 B2 | 5/2018 | Al-Zeer et al. | |
| 10,105,460 B1 | 10/2018 | Collins et al. | |
| 10,246,348 B2 | 4/2019 | Collins et al. | |
| 10,376,608 B1 | 8/2019 | Collins et al. | |
| 10,377,643 B1 | 8/2019 | Collins et al. | |
| 10,731,876 B2 | 8/2020 | Vandermeulen | |
| 10,792,608 B2 | 10/2020 | Meirav et al. | |
| 10,793,454 B1 | 10/2020 | Russell et al. | |
| 10,913,026 B2 | 2/2021 | Meirav et al. | |
| 10,921,001 B2 | 2/2021 | Allen et al. | |
| 11,083,807 B2 | 8/2021 | Ashrafi | |
| 11,110,387 B2 | 9/2021 | Meirav et al. | |
| 11,154,836 B2 | 10/2021 | Taghipour | |
| 2004/0261324 A1 | 12/2004 | Tewari | |
| 2006/0018805 A1 | 1/2006 | Yuen | |
| 2008/0099606 A1 | 5/2008 | Horstman et al. | |
| 2008/0112845 A1 | 5/2008 | Dunn et al. | |
| 2009/0311951 A1 | 12/2009 | Walkinshaw | |
| 2010/0237254 A1 | 9/2010 | Mason et al. | |
| 2011/0267805 A1 | 11/2011 | Hua et al. | |
| 2014/0263091 A1 | 9/2014 | Carter, III et al. | |
| 2015/0114912 A1 | 4/2015 | Taghipour | |
| 2015/0144575 A1 | 5/2015 | Hawkins, II | |
| 2017/0028820 A1 | 2/2017 | Walsh | |
| 2019/0009912 A1 * | 1/2019 | Matsui | B64D 13/02 |

OTHER PUBLICATIONS

Fox Mini-Eductors Fox Mini-Eductors for Aspirating, Sampling, Mixing, and Vacuum-Generation; Fox Valve Development Corp; Bulletin 401 A; https://www.grainger.com/product/4LCK2?ef_id=EAlalQobChMInpTzwrv98wIVVGxvBB0R5gqUEAQYAyABEgKM7vD_BwE:G:s&s_kwcid=AL!2966!3!496359977242!!!g!469974894180!&gucid=N:N:PS:Paid:GGL:CSM-2295:4P7A1P:20501231&gclid=EAlalQobChMInpTzwrv98wIVVGxvBB0R5gqUEAQYAyABEgKM7vD_BwE&gcl.

* cited by examiner

AIR PURIFICATION SYSTEM FOR PASSENGER TRANSPORT CABIN

BACKGROUND OF THE INVENTION

This section is intended to introduce selected aspects of the art, which may be associated with various embodiments of the present disclosure. This discussion is believed to assist in providing a framework to facilitate a better understanding of particular aspects of the present disclosure. Accordingly, it should be understood that this section should be read in this light, and not necessarily as admissions of prior art.

FIELD OF THE INVENTION

The present disclosure relates to air purification. More specifically, the disclosure relates to the treatment of air within a continuous space, such as the fuselage of an aircraft or the passenger cabin of a bus, using UV-C light. Air may also be treated in a designated indoor space or a confined outdoor space.

DISCUSSION OF TECHNOLOGY

In the travel industry, profitability is generally based upon carrying as many passengers as a transportation vessel can hold. More passengers and more routes means more revenue. To do this, airplanes, ferries, passenger rail cars, and trams carry passengers in close arrangement. In many cases, advance reservations are taken from passengers, even to the point of over-booking, helping to generate a maximum occupancy.

When a number of people are packed together in close quarters over the duration of a flight or other trip, the chances of communicating viruses or bacteria from person-to-person increases. To offset this, air filtration and circulation systems are provided. Some companies in the transportation industry pride themselves on having excellent air filtration systems. Such systems rely upon strong air flow within the cabin, typically pulling air from outside sources or internally using strong fans, moving the air through high-efficiency particulate air (HEPA) filters and towards air ducts. Air is then reintroduced into the cabin. In the case of passenger airplanes, air is typically recirculated from back to front, with fans pushing the air back towards the front of the plane. Some have said that the cleanest air on an airplane is at the back row of seats.

While HEPA filters are effective at removing small airborne particles, they cannot themselves kill pathogens. HEPA filters operate on the premise that pathogens may be trapped and then dried out, rendering them potentially incapable of infecting a host. However, it is possible for bacteria and pathogens to slip through unharmed, or to be completely reintroduced into the air ducts if the filter is disturbed.

It is known to use ultraviolet light to control pathogens. Ultraviolet light is radiation having a wavelength of about 210 to 400 nanometers. One type of ultraviolet light is "UV-C" light. Germicidal effects of UV-C light are well-established. UV-C light is a high frequency wavelength of light within the ultraviolet band. Certain UV-C light has a peak wavelength of between 210 and 290 nm and has been shown to have anti-pathogenic effects. In this respect, ultraviolet (UV) rays within the UV-C wavelength can destroy pathogens such as viruses, yeast, bacteria, mold, and mildew by breaking through the outer membrane of the pathogens. When the UV-C energy reaches the DNA/RNA of a pathogen, it causes modifications, rendering the pathogen unable to reproduce.

UV-C light may be produced artificially by a number of sources including mercury element lamps, LED, induction UV, and other technologies. Such light sources are sometimes referred to as ultraviolet germicidal lamps. Ultraviolet germicidal lamps provide a more powerful and concentrated effect of UV-C energy than can be found naturally.

Within the last few months, Honeywell has introduced a portable ultraviolet light (UV-C) system that may be rolled through the cabin of an airplane or other passenger transportation vessel. The Honeywell system is moved manually through the cabin on wheels, down the center aisle, from front to back, in order to disinfect seats and surfaces. However, the system is not designed to circulate or disinfect air. Moreover, such a system cannot be used in the presence of passengers or airline attendants due to exposure to radioactive waves.

A need exists for an air purification system that may be installed within a passenger transportation system such as aircraft, passenger railways, buses or ferries, and which disinfects air along a continuous space while the vehicle is occupied. A need further exists for an air purification system that is permanently installed into the overhead air distribution system of a passenger cabin, and which employs multiple points of air intake, filtration, purification and release. Still further, a need exists for such a system that is able to move air through the system without relying on air circulation fans while protecting passengers from UV-C rays. Finally, a need exists for a portable, self-contained air purification system that may be moved into high-traffic areas in a public building or even an outdoor space.

SUMMARY OF THE INVENTION

A UV-C air purification system for a passenger cabin is first provided. The passenger cabin is part of a transport vessel. The transport vessel may be, for example, a bus, an airplane, a passenger ferry or train.

In one embodiment, the air purification system first comprises at least one elongated air compartment. In one aspect, the elongated air compartment comprises a first compartment residing over the seats on the port side of the cabin, and a second compartment residing over the seats on the starboard side. Each compartment has a panel that is exposed to the passengers, with a plurality of openings provided along the panel.

A cavity is provided within each air compartment. Air is conveyed through the cavity and across the openings. In one aspect, the air compartment presents a single elongated air cavity that resides above a central aisle. In another aspect, a series of panels or air compartment sections are placed end-to-end in modular style. In one aspect, air is moved from a rear of the passenger cabin, towards the front through the cavity or cavities.

Each air compartment also includes a series of air filters. The air filters reside along the panel, at the plurality of openings.

The air purification system also comprises a plurality of ejector pumps. The ejector pumps are placed at selected points along the air compartment. Each ejector pump comprises an air inlet side and an air outlet side. In addition, each ejector pump includes a suction side that sealingly resides above a respective opening in the panel. The suction side draws air in from the cabin and into the air compartment, through the respective air filters.

The air purification system also includes a plurality of air tubes. Each air tube has an inlet that receives a flow of compressed air, and an outlet. The outlet is connected to the air inlet side of a respective ejector pump of the plurality of ejector pumps. The flow of air received at the inlet of each of the plurality of air tubes may be compressed air that is thiefed from an existing source of compressed air of the transport vessel.

Optionally, the air purification system also includes at least one air circulation fan. The fan is configured to pull air into ductwork residing along the cabin, and then move the air into the cavity of the at least one air compartment. Thus, the fan assists in the circulation of air across the openings.

The air purification system further provides at least one ultraviolet light emitting source. The light emitting source resides within the at least one air compartment, and is configured to disinfect air moving through the air compartment. The at least one ultraviolet light emitting source may be, for example, a fluorescent UV light, an organic light-emitting diode ("OLED"), UV induction style lamps, or an electroluminescent lamp. Preferably, the UV-C light represents a plurality of UV LED lights embedded within strips, with the strips being secured to an under-surface or interior of the air compartments within the cavity.

Optionally, a high-efficiency particulate air (HEPA) filter is provided. Preferably, the filter resides proximate an intake of the at least one air circulation fan. In one aspect, a pair of fans is provided for respective air compartments, with each fan pulling air through an associated HEPA filter. Optionally, UV-C lamps are also provided proximate the air outtake side of each of the air circulation fans.

The air purification system additionally includes a plurality of air outlets. The air outlets are placed along the panel, with each outlet being configured to release air at a selected point. The air outlets represent very small openings, sized to restrict exposure of UV-C light to passengers in the cabin. As air moves through the air compartment for disinfection, it passes through the openings so as to be distributed evenly to passengers in the cabin. In this way, a relatively continuous and even distribution of filtered and disinfected air is released into the passenger cabin.

In one aspect, the plurality of air outlets define a plurality of adjustable air nozzles. In one aspect, each of the plurality of air nozzles comprises an adjustable gasper. More preferably, the air outlets represent an array of multiple, perhaps even hundreds, of pinholes.

In one aspect, the passenger cabin comprises a plurality of seats. The seats may reside below the gaspers so that the gaspers may be accessed by passengers in the passenger cabin, and adjusted while seated. Of course, if the air outlets simply represent pinholes, no airflow adjustments would be available to the passengers.

A portable air purification system, that is, it is independent of a transportation vehicle, is also provided herein. The purification system first includes a frame structure. The frame structure comprises horizontal support members, base frame members and vertical support members. Preferably, the support members and frame members are polygonal, aluminum, tubular bodies joined together at the ends. The frame structure may be enclosed to form a tent-like structure.

The air purification system also includes an elongated air compartment. The air compartment is supported by the frame structure above a ground surface. In one aspect, the air compartment is suspended from horizontal frame members. The air compartment has an open input end and a lower panel. The lower panel may be made up of a plurality of sections hingedly connected to the air compartment, end-to-end. The lower panel includes a plurality, or matrix, of openings.

The air purification system further comprises an intake filter. The intake filter resides at an input end of the air compartment.

Additionally, the air purification system may include an air circulation fan. The air circulation fan also resides at the input end of the air compartment, and is configured to move air through the intake filter and into the air compartment.

The air purification system further comprises a series of air filters. Each of the air filters resides along the lower panel at the plurality of openings.

Additionally, the air purification system offers at least one ultraviolet light-emitting (UV-C) source. The light-emitting source resides at the input end of the air compartment. Alternatively or in addition, the light-emitting source resides within the air compartment. The UV-C light is configured to disinfect air moving through the air compartment.

The air purification system further comprises a plurality of ejector pumps. The ejector pumps reside at selected points along the air compartment, and assist in moving air through the air compartment. Each ejector pump comprises an air intake end, an air outlet end, and a suction side sealingly residing above a respective opening in the lower panel. The air tubes receive air at an inlet end from fans and/or a compressed air source. The suction side draws air through a filter in the lower panel, through the ejector pump, and into the air compartment. Air tubes deliver air to the ejector pump inlet ends from the air source.

Additionally, the air purification system includes a plurality of air outlets. The air outlets are also placed along the lower panel. Each outlet is configured to release air at selected points to provide a continuous distribution of filtered and disinfected air into the frame structure. In one aspect, the air outlets represent a matrix of small, circular through-openings, or pinholes. In another aspect, the air outlets represent slots placed along the lower panel, with each slot being placed at an angle to minimize exposure of UV-C light to individuals within the frame structure.

In a preferred embodiment, the air intake filter comprises a high-efficiency particulate air (HEPA) filter residing proximate an intake of the air circulation fan. In addition, the at least one ultraviolet light emitting source comprises a UV light, an organic light-emitting diode ("OLED"), LED strips, or an electroluminescent lamp. For example, the at least one ultraviolet light emitting source comprises a plurality of UV LED strips placed along the air compartment and above or beside the ejector pumps.

BRIEF DESCRIPTION OF THE DRAWINGS

So that the manner in which the present inventions can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

DETAILED DESCRIPTION OF CERTAIN EMBODIMENTS

Definitions

For purposes of the present application, the term "fan" refers to any air movement device. Such air movement devices may include traditional bladed fans, or may include bladeless fans such as the Air Multiplier® available from Dyson Technology LLC of Wiltshire, UK.

As used herein, the term "cabin" or "passenger cabin" refers to any compartment wherein individuals are moved. The individuals may stand, or may be seated in chairs or along benches.

The term "ejector" refers to a valve that provides motive flow for a fluid comprised primarily of air. The term ejector includes eductors, jet pumps, vacuum ejectors, air ejectors, aspirator pumps and other motive flow devices that utilize an intake side, an opposing outlet side, and a suction side, which typically is at the base of the valve. Ejectors will typically rely upon an internal design that forms a venturi tube.

As used herein, the term "train" includes traditional rail cars pulled by a locomotive engine. It also includes more modern electrically-driven cars that ride on a rail such as a subway or elevated line. It also includes so-called mag-lev trains, and the so-called Hyper-Loop that moves pods in response to pressure differential. Cars having passenger cabins may be used with any of these forms of a train. An enclosed roller coaster may also be considered a "train" for purposes of the present disclosure.

Description of Specific Embodiments

An air purification system for a passenger cabin is described herein. The passenger cabin is part of a transport vessel. The transport vessel may be, for example, a bus, an airplane, a passenger ferry, a ski lift, or a train.

Figure 1A:
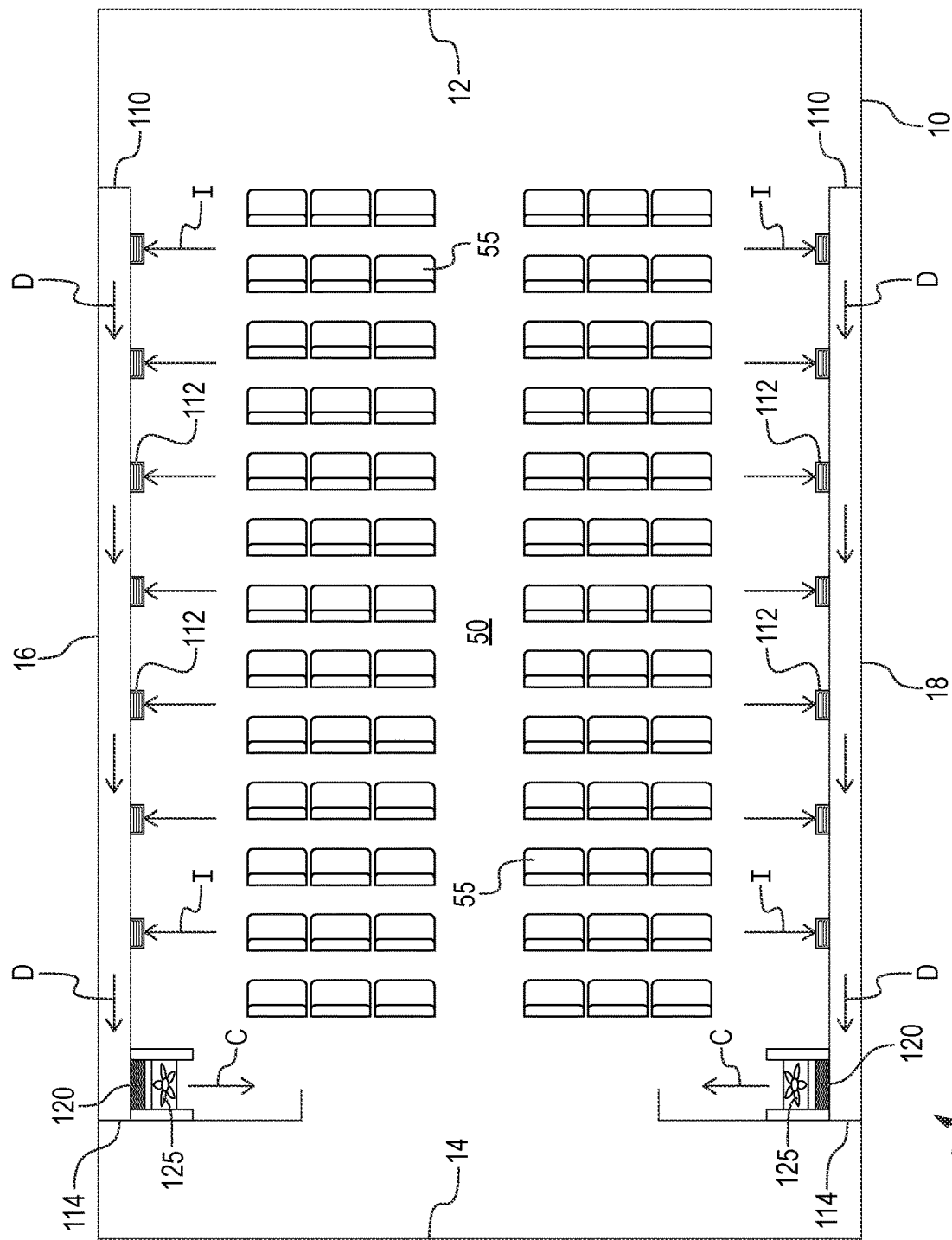
FIG. 1A is a top, or plan, view of a passenger cabin. The passenger cabin offers rows of seats for passengers. Duct work is shown on opposing sides of the passenger cabin, with air moving into the ductwork.

FIG. 1A is a top, or plan, view of an illustrative passenger cabin 10. The passenger cabin 10 offers rows of seats 55 for passengers (not shown). A center aisle 50 is provided along the rows 55. In this arrangement, six seats are shown along each row. However, it is understood that the configuration of seats is not important for the present air purification system.

The passenger cabin 10 has a front (or bow) end 12, and a back (or stern) end 14. In addition, the passenger cabin 10 has a left (or port) side 16 and a right (or starboard) side 18. The illustrative passenger cabin 10 is shown as a rectangle, but it is understood that all sides 12, 14, 16, 18 may be aerodynamically shaped. Where the passenger cabin 10 is part of an airplane, the, front 12, left 16 and right 18 sides will be concave.

The passenger cabin 10 is fitted with an air filtration system 100. Only a portion of the filtration system 100 is visible in the view of FIG. 1A. First, two series of registers 112 are visible. The registers 112 serve as air intakes, indicated by Arrows I. Air I moves through the registers 112 and into ductwork 110. The ductwork 110 resides adjacent the outermost seats, and runs along the left 16 and right 18 sides.

In the arrangement of FIG. 1A, air I moves through the ductwork 110 from front 12 to back 14, indicated by Arrows D. This is a standard direction in aircraft air circulation design. However, it is understood that the system 100 can be easily configured to move the air D from stern 14 to bow 12 or inward to the center of the airplane, it being understood that the ductwork 110 is schematic.

As the air D moves towards the back 14 of the cabin 10, the air D encounters filters 120. The filters 120 are preferably high-efficiency particulate air (HEPA) filters. Alternatively or in addition, the filters 120 are odor-reducing media such as photocatalytic oxidation filters or carbon-based filters. Each filter 120 is placed at the intake side of an air circulation fan 125. (In HVAC systems, the fan is frequently referred to as a blower, but the term "fan" is considered appropriate for this application.)

In the arrangement of FIG. 1A, two filters 120 and two fans 125 are employed. However, it is understood that additional filters 120 and fans 125 may be used. In any instance, filtered air is pushed by the fans 125, as shown at Arrows C.

As an optional feature, an ozone generating device may also be employed. Preferably, this would be placed proximate the filter 120, either at the intake or the outtake side. Alternatively, the ozone generating device may be placed at the outtake side of one or both of the fans 125. In either instance, and as demonstrated in FIGS. 1B and 1C, air C or M moves through one or more air compartments, back towards the front 12 of the cabin 10.

Figure 1B:
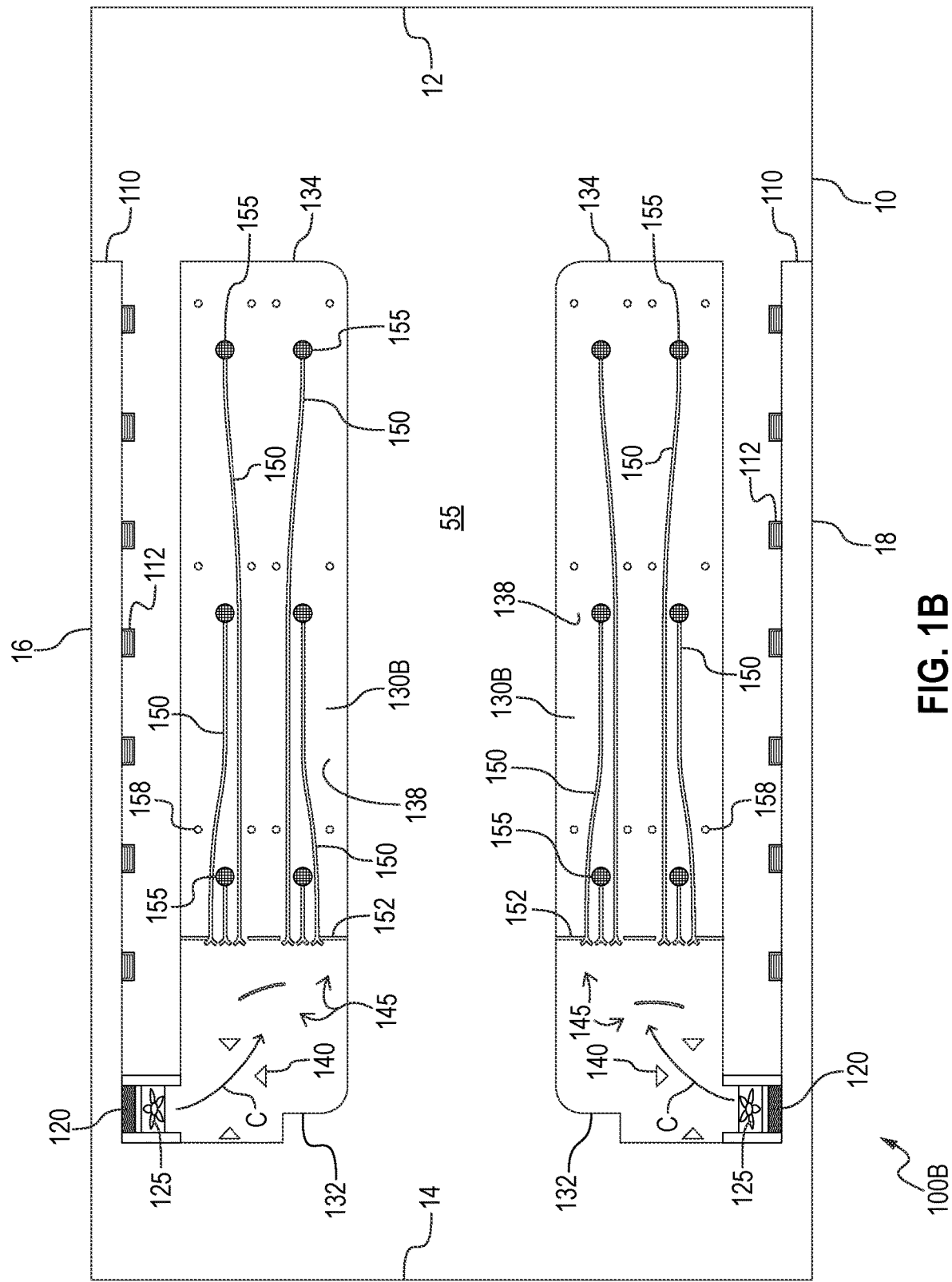
FIG. 1B is another plan view of the passenger cabin of FIG. 1A. Here, air compartments have been placed over the rows of seats. One air compartment is on the port side, while the other is on the starboard side.

FIG. 1B is another plan view of the passenger cabin 10 of FIG. 1A. FIG. 1B demonstrates additional components of the air filtration system, indicated in this embodiment as 100B. In the arrangement 100B, two air compartments 130B have been placed over the rows of seats 55. One air compartment 130B is on the port side 16, while the other air compartment 130B is on the starboard side 18. The seats 55 themselves are under the air compartments 130B and are not visible.

In FIG. 1B, it can be seen that an array of ultra-violet light emitting sources 140 is provided. As the air C leaves the fans 125, the air C is exposed to the array of lights 140. The UV lights 140 may be, for example, organic light-emitting diodes ("OLED") or electroluminescent lamps. Preferably, the UV light-emitting source is a UV-C LED with emission wavelengths in the range of 220-275 nm, but it is understood that other UV wavelengths may have germicidal properties and may be employed. There are several benefits of the UV-C LED. They consume little electricity, they are negligibly affected by numerous on/off cycles, as opposed to mercury based and other UV lamps, and they can produce effective UV energy levels at close distance. All of this makes them ideal for narrow ducts that would be installed in space-critical aircraft cabins, or other transport vehicles and safety-critical spaces. Most importantly, UV-C LED's generate radiation that inactivates bacteria, viruses, and other microorganisms.

In one aspect, the ultraviolet light source is a semiconductor device having an active layer positioned between an n-type region and a p-type region. The active layer emits radiation having a peak wavelength in a UV-C range, such as between 210 and 290 nm. A large number of UV-C LED's may be used based on GaN, AlGaN or InGaN substrates.

In any instance, the air C moves into the respective air compartments 130B and is disinfected. Each air compartment 130B has an inlet end 132 and distal end 134. Intermediate the inlet 132 and distal 134 ends is one or more panels 138. The panels 138 represent a lower surface, or other surface visible to the passengers. Of course, the panels 138 may be any panel exposed to the passengers in the cabin 10.

A plurality of air outlets 158 reside along the panels 138. Each outlet 158 is configured to release air C as the air C moves from the inlet end 132 towards the distal end 134. In this way, a relatively continuous and even distribution of filtered and disinfected air is circulated into the passenger cabin 10.

As an optional feature, the air compartments 130B may include sets of "internals" 145. The internals represent partial barriers to the flow of air C into or through the air compartments 130B. The internals 145 serve as diverters, and help ensure that the air is mixed and exposed to the UV-C lights 140 for an adequate time for disinfection. In one aspect, and particularly where UV-C LED strips 342 are placed along the air compartments 130B, the internals 145 may also reside in the air compartments 130B.

In addition to the air outlets 158, the air compartments 130B also include openings 155 placed along the panels 138. The openings 155 are configured to receive air from the cabin 10. Filters (shown at 135 in FIGS. 2A and 2B) are preferably placed in the openings 155 to further filter the circulated air C.

The air filtration system 100B also includes air tubes 150. Each air tube 150 has an inlet 152 that is fluid communication with a source of air flow. The source of air flow M may be taken, for example, from compressed air already available incident to turbines, pumps, or braking systems on the transport vessel. Alternatively, the source of air flow C may be from the air circulation fans 125, wherein a portion of the air C flows into the air tubes 150, at inlets 152, while the rest of the air C flows into the air compartment 130B by action of the fans 125 to aid in the movement of air C. In a preferred embodiment, the system 100 moves air using only compressed air delivered directly into the air compartments 130B.

Beneficially, the flow of air through the tubes 150 is aided by motive air flow. Ejectors (or "ejector pumps"), shown at 250 in FIGS. 2A and 2B) are placed along the lengths of the tubes 150. The inlet tubes 150 cause the ejectors 250 to pull air from the cabin 10 and into the air compartments 130B, further pushing the air towards the distal end 134 of the air compartments 130B. The ejectors 250 are spaced close enough to each other to generate a good mix of the air F through the air compartment 130B, but spaced apart at sufficient intervals so as not to overpressure the duct, causing the air to exit before it has had adequate time for disinfection.

One preferred ejector pump is the Fox™ Mini-Ejector. This ejector pump is available from Fox Development Corporation of Dover, New Jersey. Of course, other ejectors may be used.

Figure 1C:
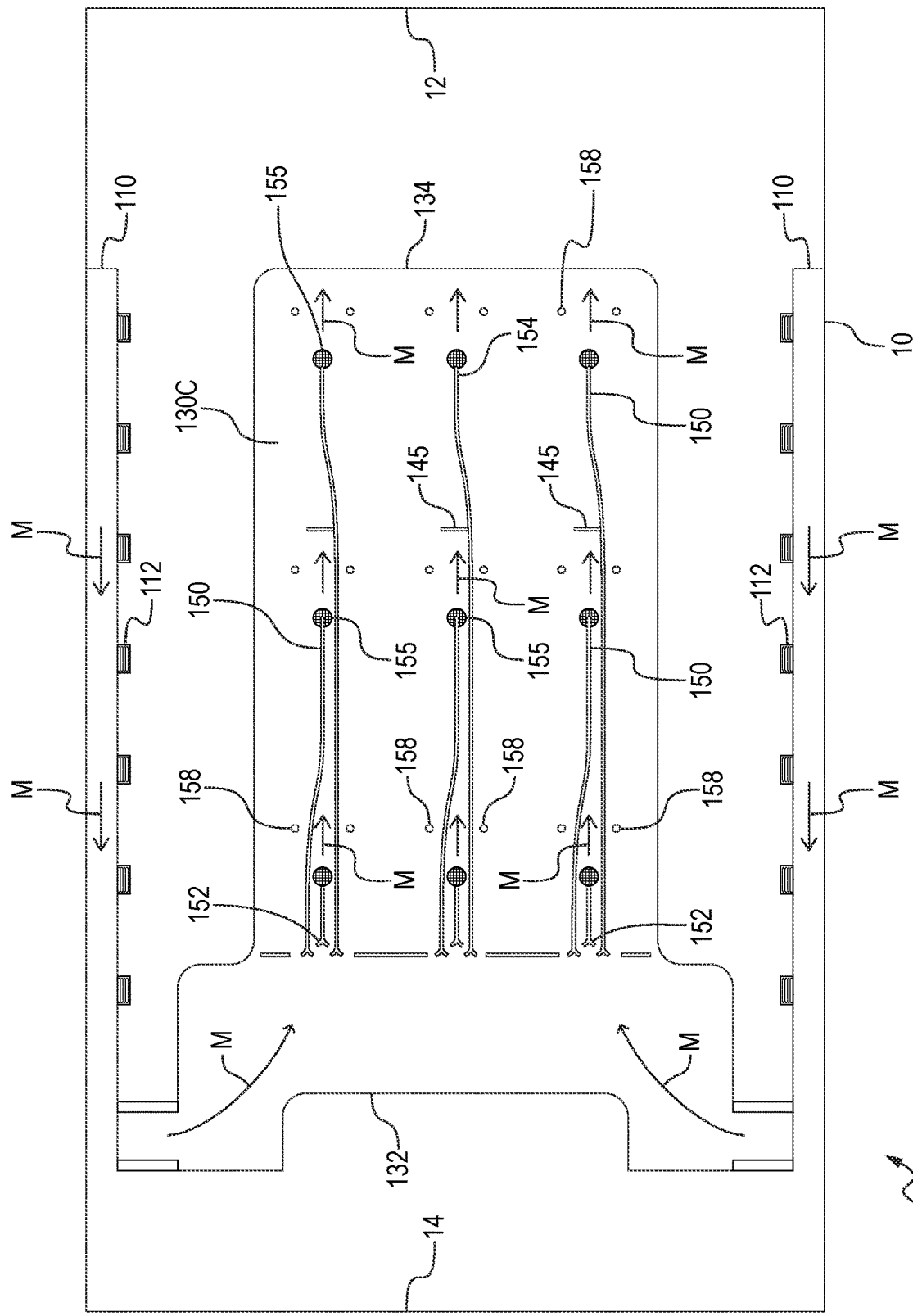
FIG. 1C is an alternate plan view of the passenger cabin of FIG. 1A. Here, a single air compartment has been placed over the seats, with the air compartment generally residing over a center aisle.

FIG. 1C is an alternate plan view of the passenger cabin 10 of FIG. 1A. Specifically, FIG. 1C demonstrates components of an alternate air filtration system, indicated as 100C. In the arrangement 100C, a single air compartment 130C has been placed over the rows of seats 55, with the air compartment 130C generally residing over the center aisle 50 (not visible). The air compartment 130C is generally structured in accordance with the air compartments 130B discussed above, with like elements being consistently numbered, except that motive air M is used rather than air C circulated through registers 112 and fans 125.

Figure 1D:
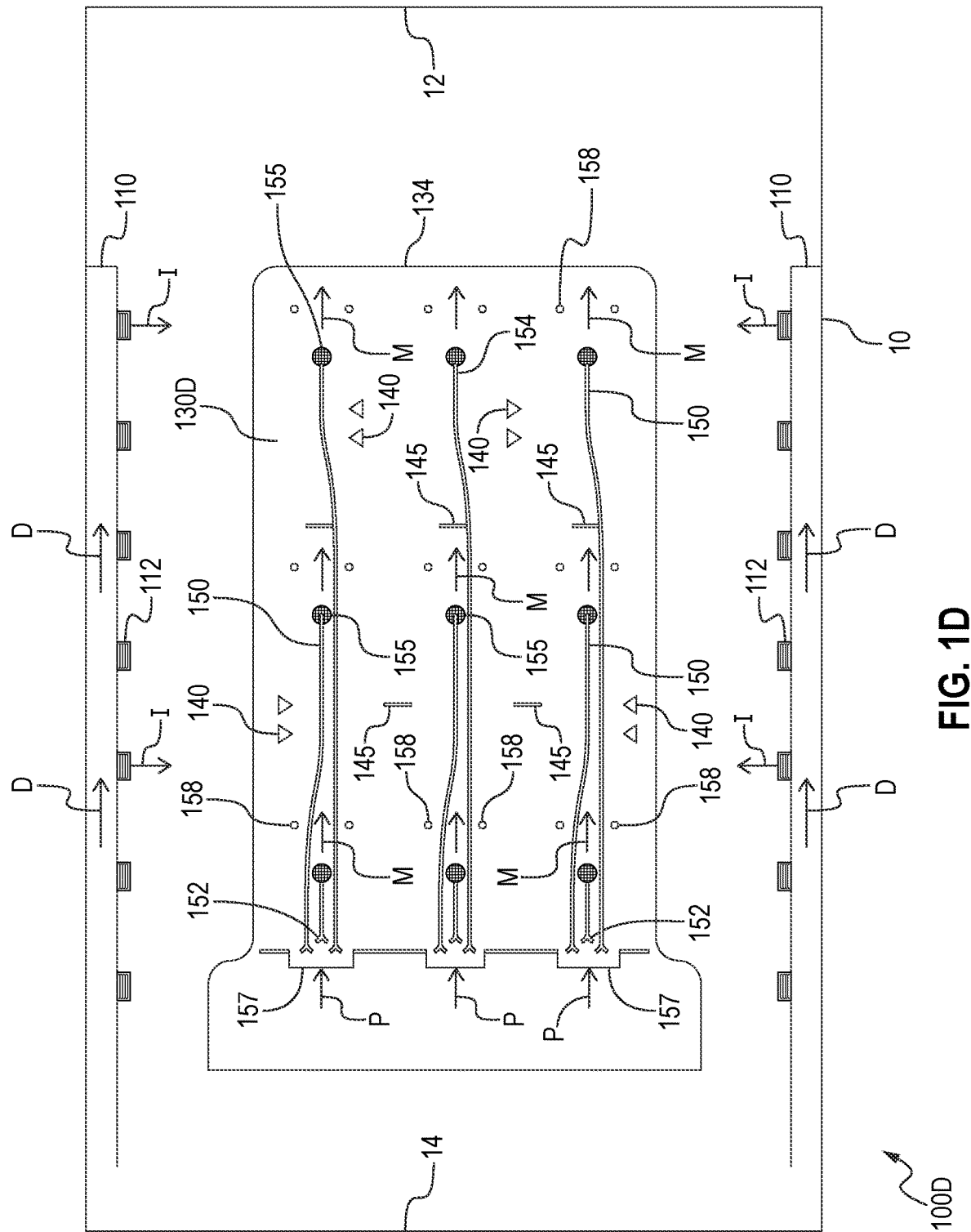
FIG. 1D is yet another plan view of the passenger cabin of FIG. 1A. As with FIG. 1C, a single air compartment has been placed over the seats, with the air compartment generally residing over a center aisle. Compressed air is pumped into the air tubes.

FIG. 1D is yet another plan view of the passenger cabin 10 of FIG. 1A. FIG. 1D demonstrates components of an alternate air filtration system, indicated as 100D. As with FIG. 1C, a single air compartment 130D has been placed over the rows of seats 55, with the air compartment 130D generally residing over a center aisle (again not visible). Compressed air is pumped into the air tubes 150 by means of air that is compressed by existing turbines or pumps on the transport vessel. The pumped air is shown at Arrows P. The pumped air P is independent from the air D that is circulated through the registers 112 and air ducts 110.

In FIG. 1D, three pressurized air manifolds 157 are shown. The manifolds 157 are configured to disperse pressurized air P to the plurality of air tubes 150. The manifolds 157 are in fluid communication with air inlets (shown at 152 in FIG. 2C) of the various air tubes 150. The air P is thiefed from an existing source of compressed air, such as from an air compressor or, more preferably, from compressed air generated by and readily available from turbines, pumps, a hydraulic system or a braking system on the transport vessel. Additional details concerning the manifolds 157 is provided below in connection with FIG. 2C.

It is observed that UV-C lights 140 are placed within the air compartment 130C. As noted above, the UV-C lights 140 generate radiation that inactivates bacteria, viruses, and other microorganisms. In addition, internals 145 have been placed along the air compartment 130D. As described above, the internals serve to impede the flow of air, allowing the air to be more fully exposed to the UV-C lights 140 as it flows from the various air tubes 150 through the air outlets 158 along the air compartment 130D.

Figure 2A:
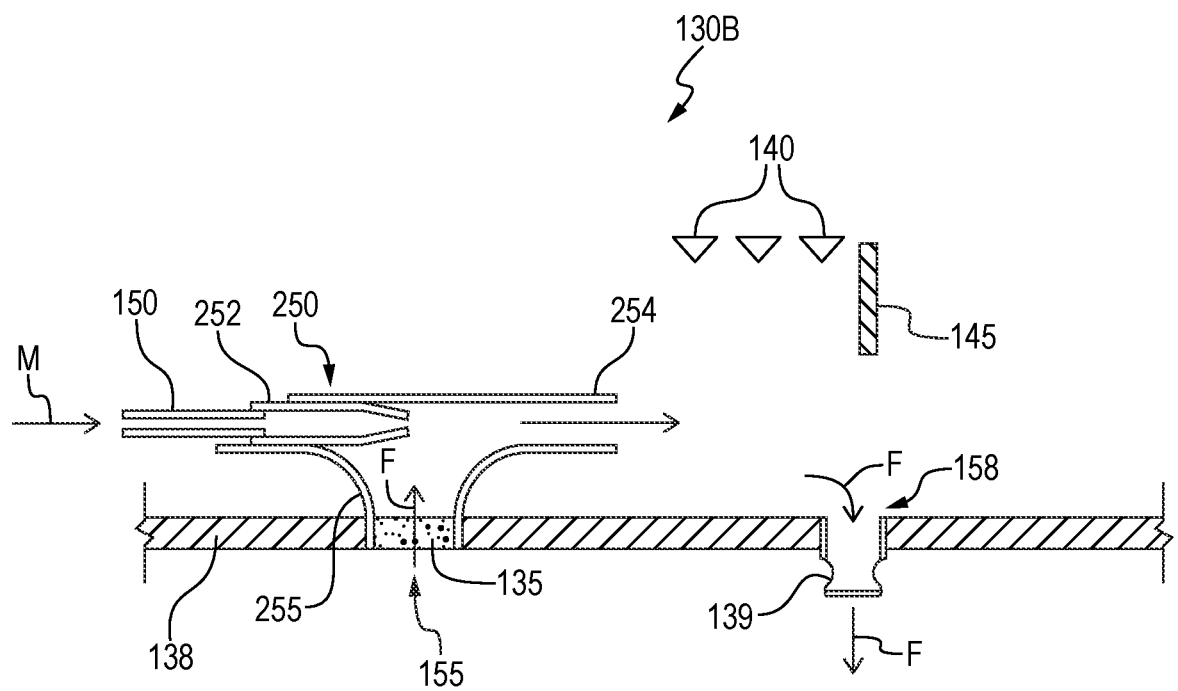
FIG. 2A is a side, cross-sectional view of a panel of one of the air compartments of FIG. 1B. An ejector is shown residing over a filter in the lower panel. A gasper is shown at the lower panel as an air outlet.

FIG. 2A is a side, cross-sectional view of a panel 138 of one of the air compartments 130B of FIG. 1B. In this view, an opening 155 in the panel 138 is visible. The opening 155 serves as an air inlet, with Arrow F indicating a flow of air into the air compartment 130B. A filtration medium 135 is affixed within the opening 155. As air F moves through the opening 155, the air is filtered.

FIG. 2A also shows an air outlet 158. Air F flows from the air compartment 130B and back into the cabin 10, through the air outlet 138. As shown in FIG. 1B, the air compartment 130B actually offers multiple air openings 155 and multiple air outlets 158. Ideally, the air outlets 158 are essentially pinholes formed in a matrix. In this way, clean air is distributed evenly throughout the cabin 10.

It is noted that in the arrangement of FIG. 2A, the air outlet 158 is in the form of a nozzle. More specifically, the air outlet 158 is in the form of an air gasper 139. The gasper 139 allows passengers to adjust the amount of air that is flowing through the outlet 158.

In order to move the air F along the air compartment 130B, and as indicated above, a series of ejectors 250 is employed. FIG. 2A demonstrates an ejector 250, in one embodiment. The ejector 250 has an air inlet 255 that is in sealed fluid communication with the opening 155. Air F is drawn in through the filtration medium 135 and into the ejector 250.

The ejector 250 has a tube inlet end 252 that is in sealed fluid communication with an air tube 150, and a tube outlet end 254. As shown, the tube inlet end 252 receives pressurized air M through an air tube 150 (seen more fully in FIG. 2C). The tube outlet end 254 releases air from the ejector 250. The ejectors 250 use pressurized (or "motive") air through inlet end 252 and over a venturi and convergent and/or divergent internals to create pressure differential, which draws air F into the ejector 250, and moves the air F into the air compartment for disinfection, and on towards downstream air outlets 158. In this way, the ejector 250 serves as a motive flow valve operated by small, relatively high pressure lines 150 of preferably conditioned air.

Figure 2B:
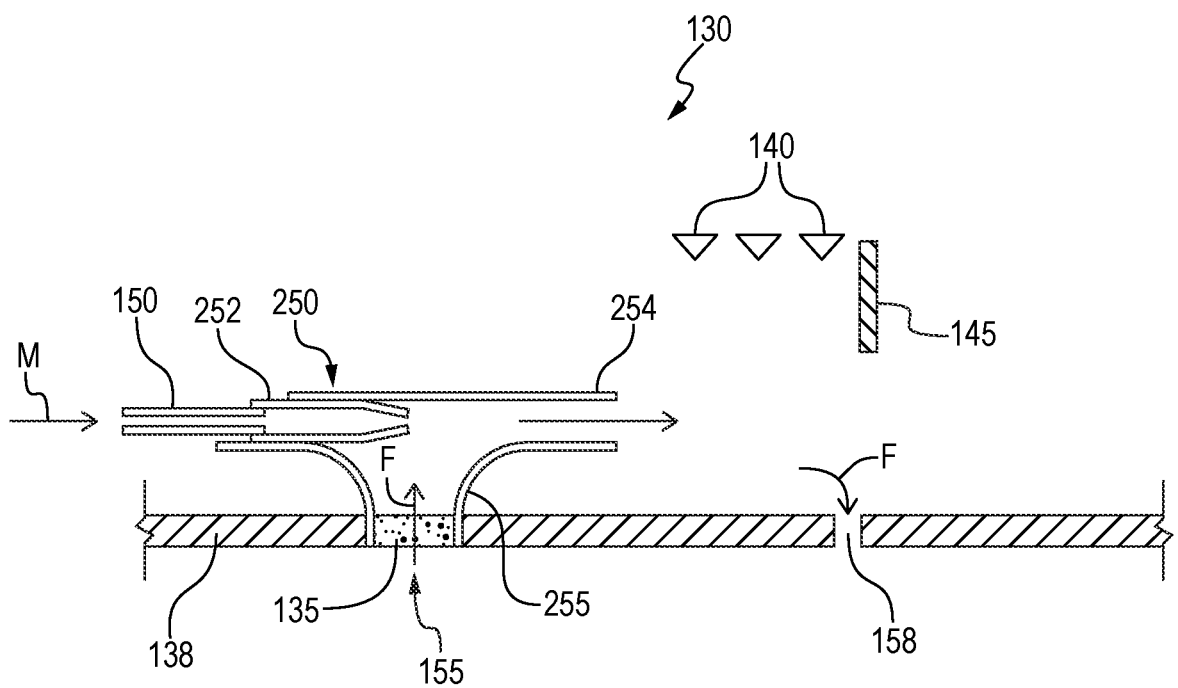
FIG. 2B is a side, cross-sectional view of the panel of the air compartment of FIG. 1C. An ejector is shown residing over a filter in the lower panel. A small pinhole-type opening is also shown as an air outlet.

FIG. 2B is a side, cross-sectional view of the panel 138 of the air compartment 130C of FIG. 1C. The ejector 250 is again shown residing over the filter 135 in the air inlet 155. In addition, a small outlet 158 is shown as the air outlet. Ideally, a matrix of very small openings 158 is placed along the lower panel 138. The outlets 158 (and any optional adjustable outlet nozzles 139) are sized to prevent exposure of UV-C light to passengers. For example, each air outlet may only be 0.25 cm in diameter, or 0.1 cm in diameter, or less. There could be a matrix of 100, or 200, or 500, or even more, pinhole-type openings 158 in the panel 138.

UV-C light, particularly in the 253-270 nm wavelength range, is proven to be highly effective for germicidal irradiation. However, it is not safe for continuous exposure to the skin or eyes of humans, so in many environments potential human exposure precludes its use. By providing multiple small outlets 158 that are spaced apart, the system will safely and actively disinfect the air in spaces with human occupants. The desired level of disinfection can be accurately achieved for broad or specifically targeted pathogens by calculating the UV need based on the device dimensions, material used, and the expected time of exposure. Most harmful virus and bacteria in the air passing through this device can be disinfected in under one second with proper air chamber sizing and airflow calculations.

In addition to the UV-C lights, the panel 138 may also include visible light-emitting sources. Any type of light from the bottom-visible, or 222 nm UV-C, may be added.

Figure 2C:
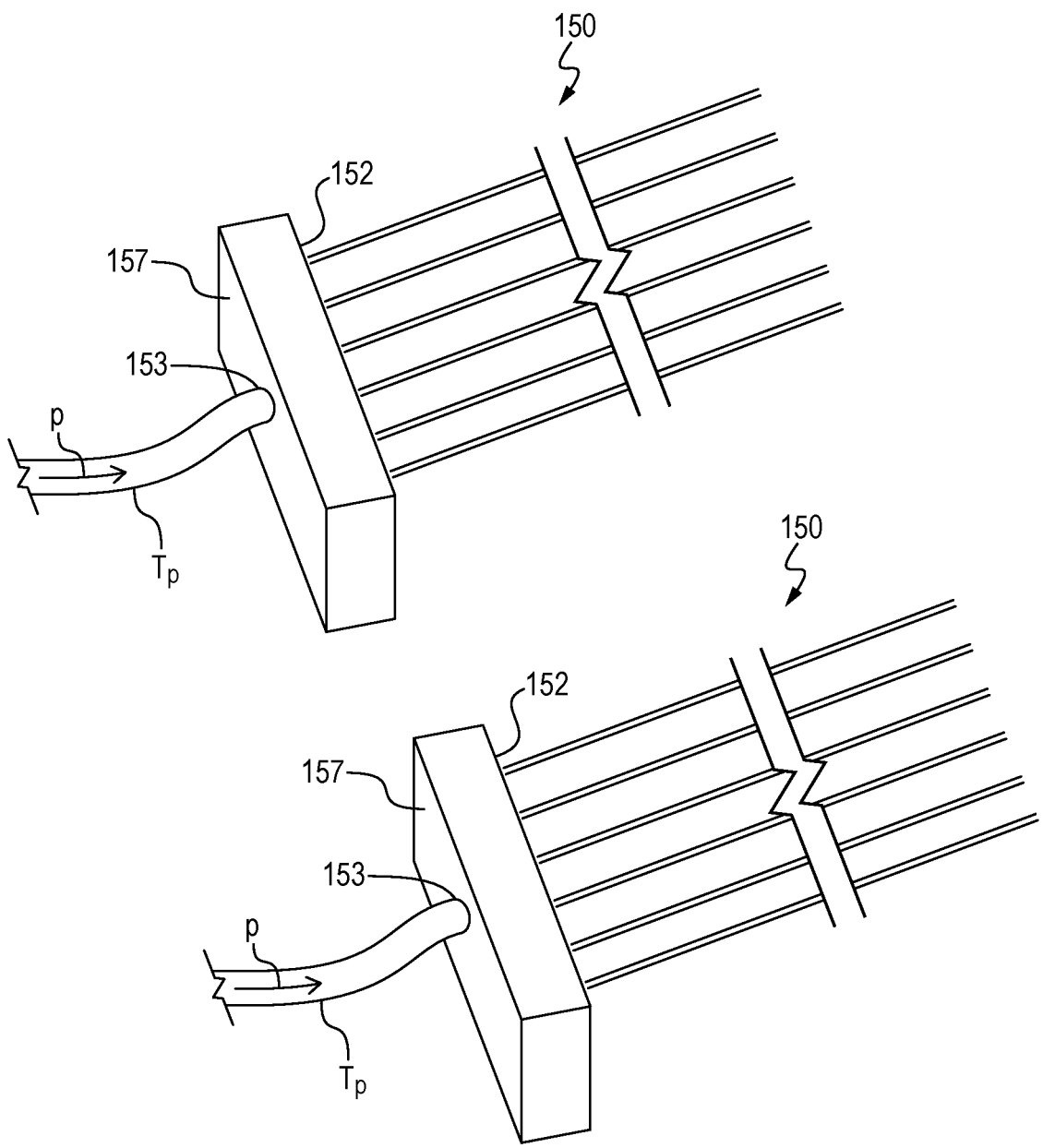
FIG. 2C presents two pressurized air manifolds. The manifolds disperse pressurized air to the plurality of air tubes.

FIG. 2C presents two pressurized air manifolds 157. The manifolds 157 are configured to disperse pressurized air P to the plurality of air tubes 150. An air tube Tp carrying pressurized air P feeds into an inlet 153 of each manifold 157. The manifold 157 is in fluid communication with the air inlets 152 of the various air tubes 150. The air P is thiefed from an existing source of compressed air, such as from an air compressor or, more preferably, from compressed air generated by and readily available from turbines, pumps, a hydraulic system or a braking system on the transport vessel. In a preferred embodiment, air supplied into the air compartments comes only from the compressed air and the ejectors 250, without the use of air circulation fans 125 or even the intake ductwork 110.

Figure 3:
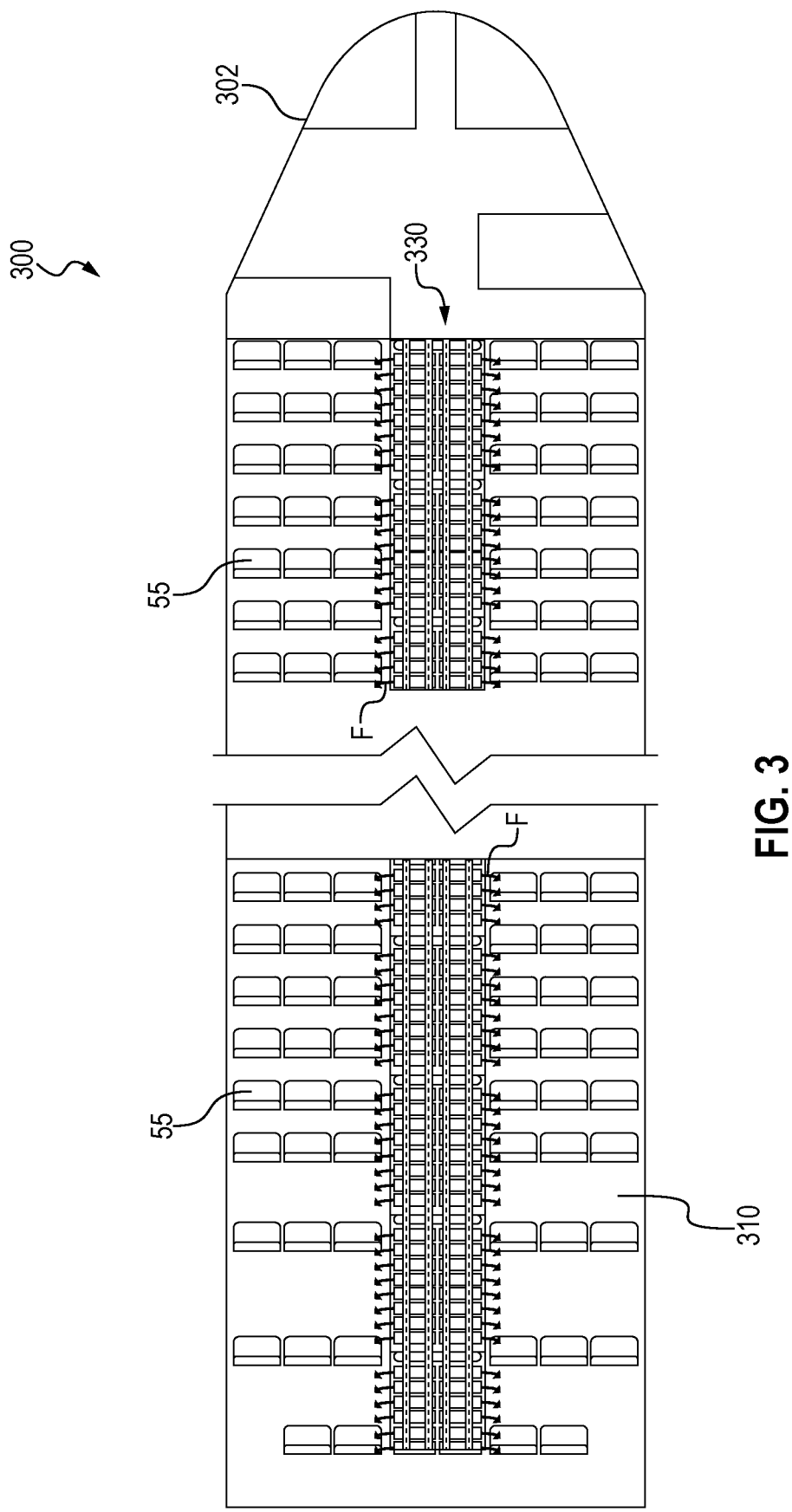
FIG. 3 is a plan view of the passenger cabin, or at least a portion of the passenger cabin, of an airplane. An elongated air compartment is shown along the aisle of the passenger cabin.

FIG. 3 is a plan view of a passenger cabin 310, or at least a portion of a passenger cabin 310, of an airplane 300. An elongated air compartment 330 is shown. The air compartment 330 is generally in accordance with air compartment 130C of FIG. 1C, but with modifications as set out in FIGS. 4A and 5A below. The passenger cabin 310 includes a number of seats 55 arranged in rows, with the air compartment 330 extending along the aisle of the passenger cabin 310. The air compartment 330 is arranged in modular form. Arrows indicate an outflow of air from the air compartment 330.

Figure 4A:
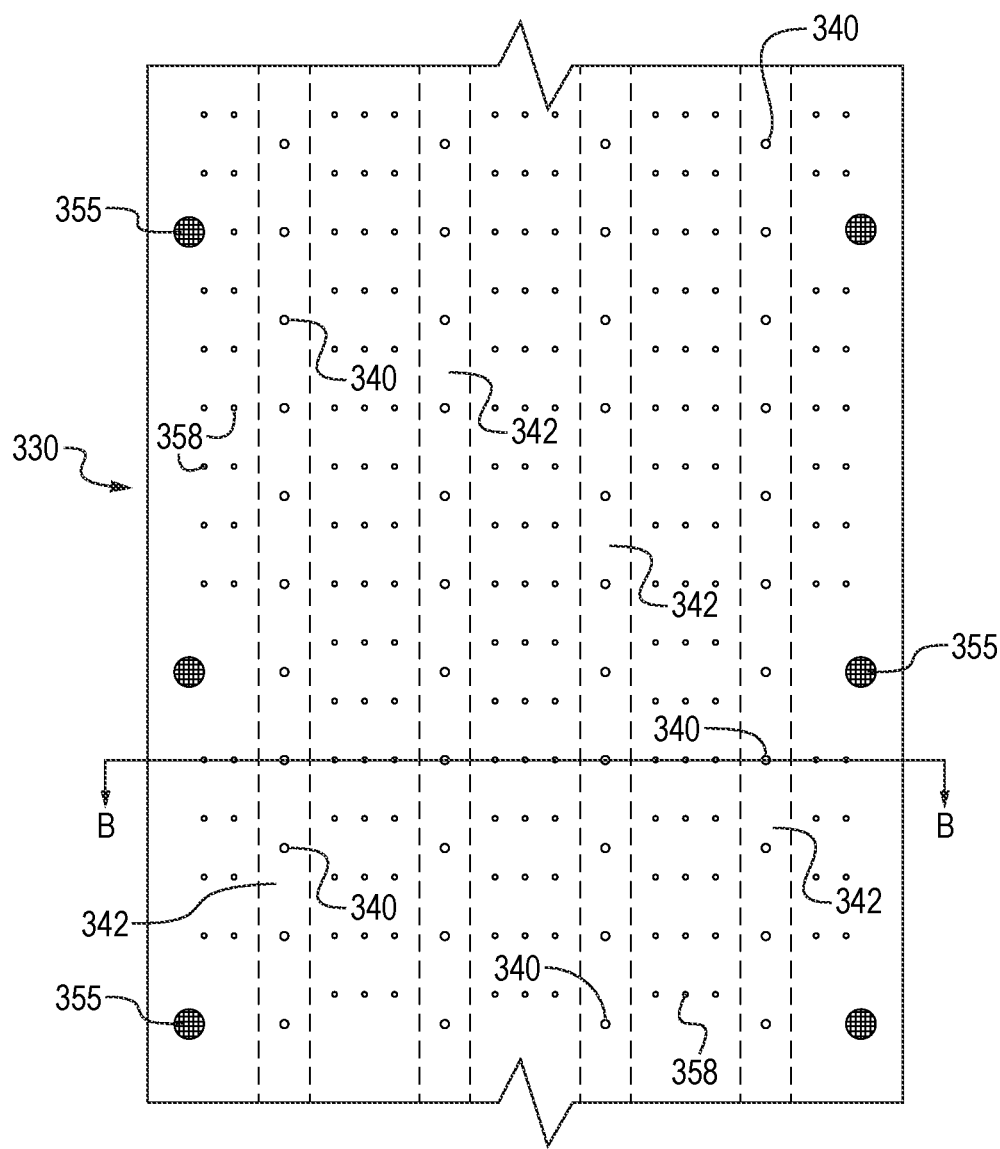
FIG. 4A is a bottom view of an enlarged portion of the air compartment of FIG. 3. This may represent one of many modules intended to be connected end-to-end.

FIG. 4A is a bottom view of an enlarged portion of the air compartment 330 of FIG. 3. It can be seen that the air compartment 330 includes a matrix of air inlets 355. Each air inlet 355 includes a filtration medium, such as shown at 135 of FIGS. 2A and 2B. In addition, the air compartment 330 includes a matrix of small air outlets 358. The air outlets 358 are also shown in the cross-sectional view of FIG. 2B. The air outlets 358 are in the form of very small pinholes, each having a diameter of less than 0.25 cm, and more preferably less than 0.1 cm, or even less than 0.05 cm.

The air compartment 330 also includes a series of UV-C strips 342. The UV-C strips 342 may be in the form of LED light strips. In one aspect, the strips 342 offer 18 ultraviolet LED's 340 per meter, with the strips 342 being placed about four inches apart. The number and spacing of the strips 342 depends on the width and depth of the air compartment 330, the flow rate of the air M, the targeted pathogens, and the UV output of the LED lights 340. The LED's 340 may provide, for example, 265 nm light wave frequency.

The UV-C energy from the ultraviolet light sources 340 is designed to kill viruses, bacteria and mold in the air as the air C, F, M, P moves through the air compartment 330 from an inlet end 132 to a distal end 134. Ultraviolet producing light emitting diode devices (LED's) are preferably utilized for the UV-C irradiation for their compact design, durability and low power requirements.

Figure 4B:
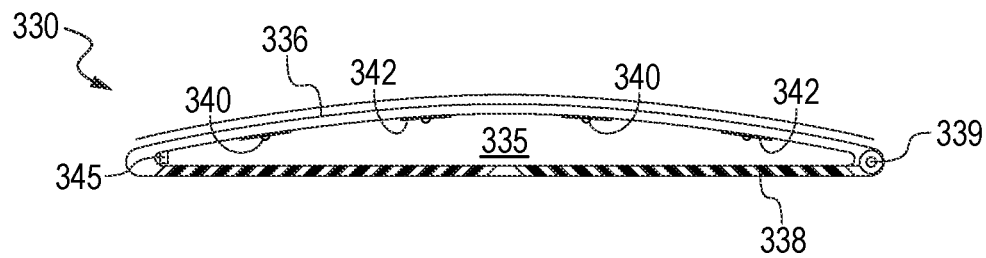
FIG. 4B is a cross-sectional view of the air compartment of FIG. 4A, cut across Line B-B.

FIG. 4B is a cross-sectional view of the air compartment 330 of FIG. 4A. The view of FIG. 4B is taken across Line B-B. In this arrangement, the air compartment 330 is a self-contained compartment that has an upper, concave housing 336, and then a lower panel 338. The lower panel 338 is connected to the housing 336 through hinge 339. Together, the housing 336 and the panel 338 form an internal cavity 335.

It is noted that the internal cavity 335 may receive conditioned air. Conditioned air may mean air that has been heated, refrigerated, vaporized or dehumidified. In this instance, the internal cavity 335 may be used as a duct for conditioned air. Preferably, the under surface of the housing 336 is either made of or is lined with a reflective, UV-resistant material to enhance the treatment of the conditioned air.

In FIG. 4B, four UV-C light strips 342 are shown attached to an undersurface of the housing 336. LED lights 340 are connected to the light strips 342. Alternatively, the lights 340 represent semiconductors. The UV-C light strips 342, in turn, are connected to the electrical system of the airplane. The LED lights 340 also commonly emit a small amount of visible light which will illuminate the cavity 335 of the air compartment 330, while the UV-C is disinfecting the cavity 335 and disinfecting the air F. Beneficially, this visible spectrum may be seen through the outlets 358, 158, 139, and serve as a reminder to the passengers of the pathogen-reducing mechanism in place as well as add a safety layer to prevent maintenance personnel from accessing powered air disinfection panels.

Optionally, a switch 345 is provided in the cavity 335. The switch 345 senses when the lower panel 338 is opened, and automatically turns off the UV-C lights 340.

It is observed that in the arrangement of FIGS. 4A and 4B, no ejectors are used. Instead, air C is moved through the cavity 335 by means of the fans 125 of FIG. 1A only. Alternatively, the air C may be moved by taking advantage of compressed air already available incident to any turbines or pumps used for other purposes. However, it is understood that ejectors 250 may be placed over the filters of openings 355, or alternatively one-way air flow valves may be used.

Figure 5A:
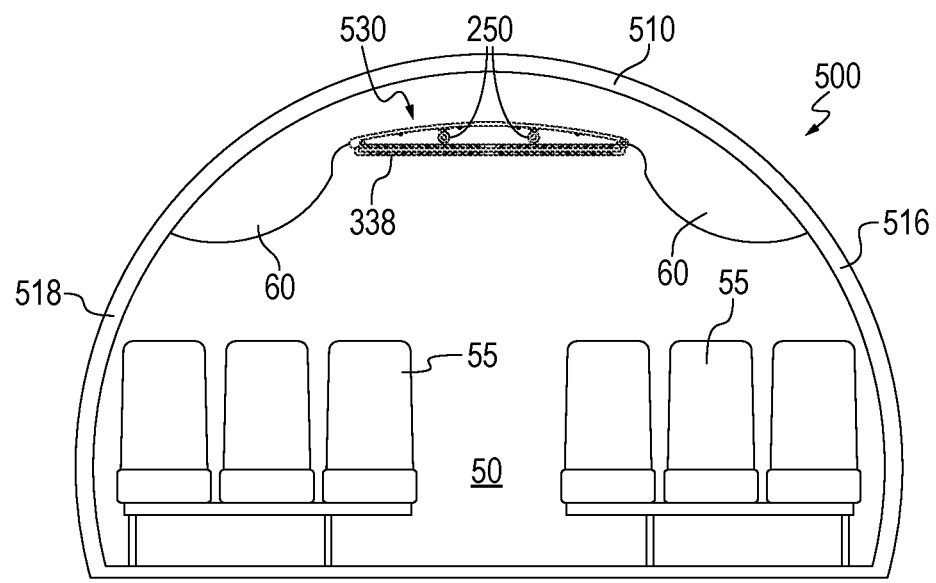
FIG. 5A is a cross-sectional view of a passenger cabin of a rail pod. An exemplary air compartment is shown above the center aisle, in cross-section.

FIG. 5A is a cross-sectional view of a passenger cabin 500 of a rail pod. While the passenger cabin 500 is intended to be a rail pod, it is understood that it could be any other type of passenger cabin. The rail pod may be associated with a train that runs on magnetic levitation. Alternatively, the pod may operate using electricity or may move in response to pressure differential within a confined tube or tunnel. The cabin 500 has a concave housing 510 for aerodynamic purposes. The housing 510 includes a port side 516 and a starboard side 518.

In the arrangement of FIG. 5A, six seats 55 are shown. A center aisle 50 is preserved between the seats 55. It is understood that the cabin may offer multiple rows of seats 55. Overhead compartments 60 are shown schematically above the seats 55.

An air compartment 530 is shown above the center aisle 50. The air compartment 530 is generally in accordance with the air compartment 330 of FIG. 4B, except that the lower panel 338 has two parallel layers. The additional layer provides a level of insulation between passengers and the UV-C lights 340. In addition, air compartment 530 utilizes the ejectors 250 to assist in moving air through the cavity 335. The ejectors 250 are shown in equi-distantly spaced, side-by-side arrangement, but it is understood that ejectors may be installed in groups of more or less than two and may or may not be symmetrically arranged.

The benefit of placing the air compartment 530 above the center aisle is that little to no modification of existing overhead luggage bins is required. The array of gaspers, attendant buttons, safety signs, oxygen masks, and no smoking signs, etc. need not be changed. The compartment 530 can also be easily retrofitted for use in airplanes, subways, busses, rail cars, and even moving walkways.

Figure 5B:
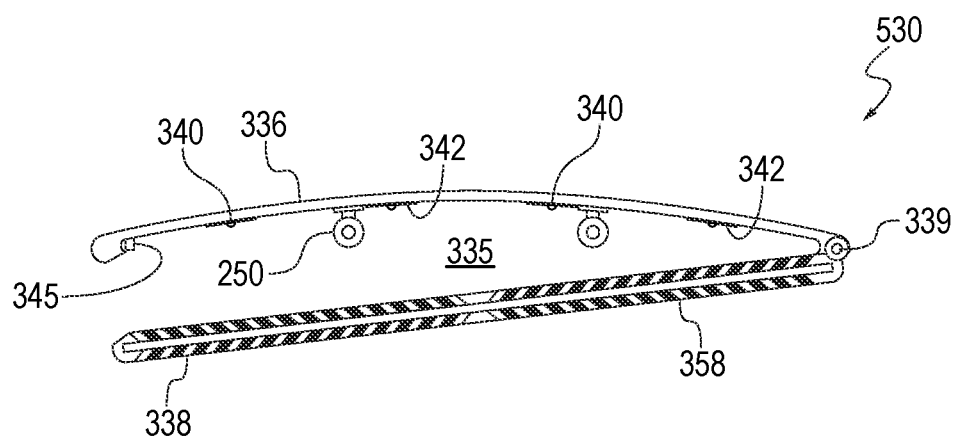
FIG. 5B is an enlarged view of the air compartment of FIG. 5A. Here, the panel of the air compartment has been opened, demonstrating that a cavity of the air compartment may be accessed for maintenance purposes.

FIG. 5B is an enlarged view of the air compartment 530 of FIG. 5A. Here, the panel 538 of the air compartment 530 has been released. This demonstrates that the cavity 335 of the air compartment 530 may be accessed for maintenance purposes. For example, maintenance may need to replace a UV-C light strip 342. Again, the switch 345 serves to disable the lights 340 along the light strips 342 in the event that the panel is opened without first manually turning off or otherwise disabling the UV-C lights 340. It is understood that the switch 345 may be installed in a variety of locations in order to accomplish its safety function.

It is again observed that the lower panel 338 includes a plurality of air outlets 358. The outlets 358 are designed to release disinfected air into the cabin 500 in a continuous, low-flow fashion. The outlets 358 are designed to be small enough to prevent direct exposure to unacceptable levels of UV light 340 exposure.

As can be seen from the drawings and the above discussion, an improved air filtration system for a passenger cabin is offered. The system directs moving air from multiple inlet locations along an air compartment through a panel, where it receives UV exposure for disinfection. The system allows for a series of connected air compartment sections to be installed for disinfection coverage over selected lengths. Beneficially, the system is able to actively mix and disinfect air in a continuous method over potentially very long distances while occupants are in close proximity.

The air is moved through the air compartment sections using compressed air, vacuum, fans, motive flow valves, or combinations thereof, all while being disinfected through a highly effective dose of ultraviolet light. The treated air is then returned to the occupied passenger space through a matrix of air outlets along the length of the duct. Thus, potentially contaminated air is drawn in, quickly disinfected, and returned to the space through even distribution.

In a preferred embodiment, the passenger cabin is a part of an aircraft, where air compartments are installed above the seats or aisles in such a way that signage would not need to be altered. The air compartments have a low profile so as to avoid or limit restrictions to passenger head room, overhead baggage bins or emergency equipment compartments. The modular (or segmented) nature of the long, ducted air compartments allows for quick maintenance access to replace UV-C lights, filters, ejectors, or for cleaning.

Preferably, the air filtration systems herein utilize small volumes of air compressed and then pushed through so-called ejector pumps. As air moves across the ejectors, additional air (including vaporized fluid) is drawn from the cabin and into the air compartments. The air is then disinfected by one or more UV lights before the higher pressure inside the chamber drives the air or vapor through a multitude of exit points along the length of the compartment, or overhead duct. Where air circulation fans are not used, the system will have no moving parts other than movable or hinged access panels for maintenance, or the source of compressed air.

The air filtration system may be incorporated into buildings such as airports or indoor shopping malls where heavy pedestrian traffic occurs. In this instance, air compartments having air tubes, air inlets, filters, ejectors and air outlets may be installed into ductwork in selected portions of the building. Air outlets would be placed in ceiling panels or air purification panels, with air being supplied by a source of compressed air, aided by motive air flow, or fans. The system may also be modified for use in outdoor high-traffic areas such as ticket lines or concession areas for a sporting venue.

As an alternate arrangement to the air filtration systems 100B, 100C (and variations) disclosed above, a free-standing and portable system is also disclosed herein. The portable system is intended to be used at large public venues such as concert halls, sporting arenas and stadiums where individuals might congregate. Examples of such areas include ticket lines, restroom lines and concession stands.

Figure 6:
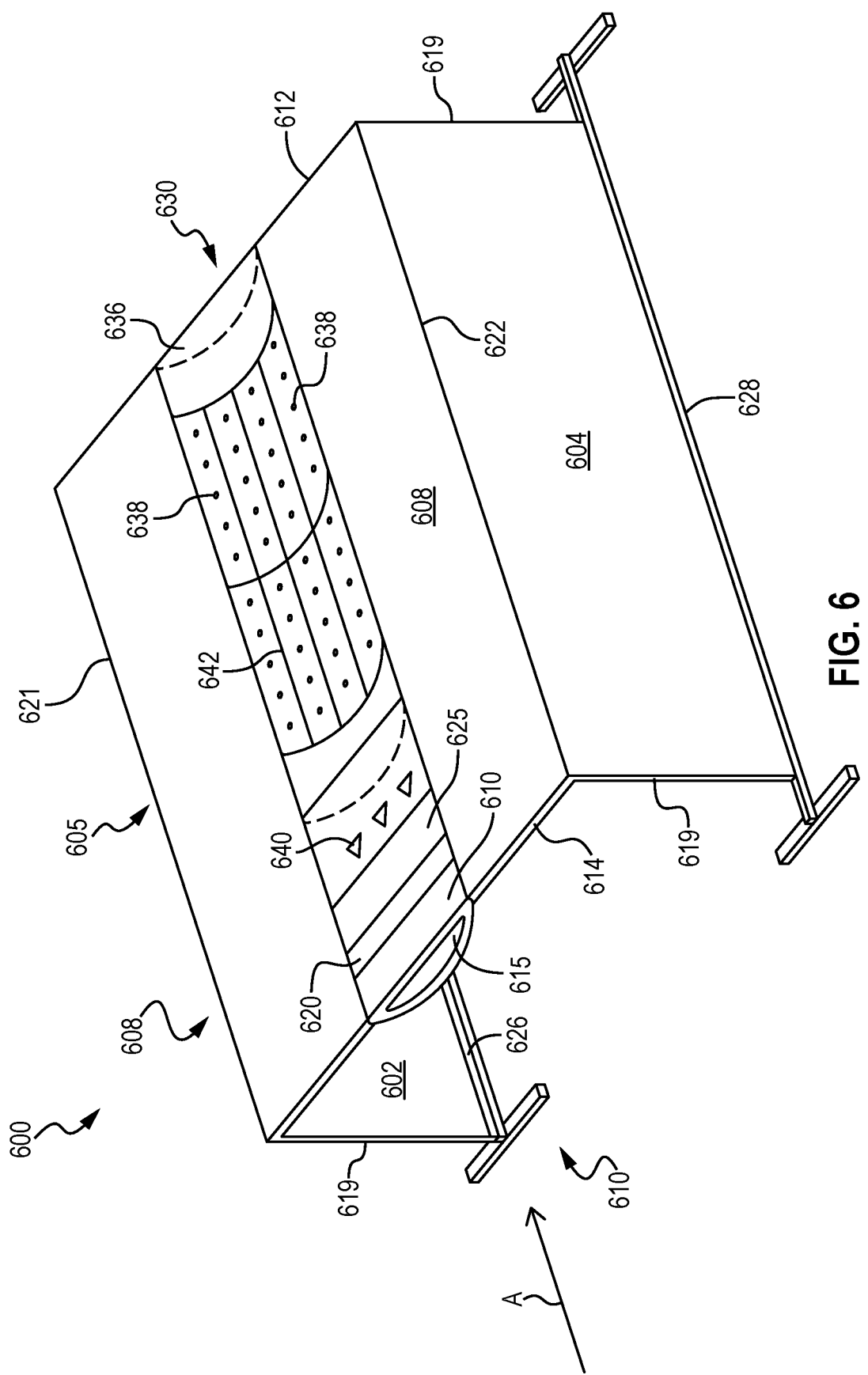
FIG. 6 is a perspective view of a free-standing air purification system of the present invention, in one embodiment. This serves as an alternative to the air purification systems described in other figures, wherein the system is incorporated into a passenger cabin for a transport system.

FIG. 6 is a perspective view of a free-standing air filtration system 600 of the present invention, in one embodiment. The air filtration system 600 represents a partially enclosed structure 605 having a front end 612 and a back end 614. Air A is directed from the back end 614 to the front end 612 of the structure 605. Individuals will enter the structure 600 at the back end 614. The ticket counter, restroom, or food service counter will be at the front end 612 of the structure 605.

The structure 605 may have an open top, or may be covered, or it may be completely enclosed. In the arrangement of FIG. 6, the structure has a cover 608, which is preferably fabricated from a lightweight plastic material. The structure 605 also includes optional left 602 and right 604 sides, or panels. The sides 602, 604 are also preferably fabricated from a plastic material. The plastic material holds in purified air generated by the air purification system 600.

Base frame members 626, 628 are provided to support the structure 605. In addition, a frame system 618 is provided to support the cover 608 and sides 602, 604 above the base frame members 626, 628. These include horizontal support members 621, 622 above the base frame members 626, 628 and vertical support members 619. The frame system 618 may include wheels or slidable pucks or feet to provide portability.

The air purification system 600 includes an air inlet 610. Air A is drawn into the inlet 610 through opening, or cavity 615. Air A then moves through the system 600 for treatment. Components of the air purification system 600 may include a HEPA filter 620, a fan 625, UV-C emitting light sources 640, and an air compartment 630. The air compartment 630 may be designed generally in accordance with the compartments of FIG. 4B or 5B. To this end, the compartment 630 will include air inlets (not shown), optional ejectors (not shown), air outlets 655, and UV-LED light strips 642.

Individuals attending a public event or visiting a high-concentration public space will receive air that has undergone rapid disinfection. A separate local compressor or other source may be used to drive ejector pumps and/or power for UV devices and optional fans. However mechanical fans or other air movement device could adequately operate the system 600.

In an alternate geometry, the frame structure 605 is concave, and may have the profile of a Quonset hut. The cavity 615 may be semi-circular in profile and may extend across a substantial portion of the Quonset hut. Air inlets with ejector pumps may be dispersed radially along the cavity 615 of the frame structure 605. Hundreds of pinhole air outlets may be placed along the cavity 615 as well, essentially surrounding individuals as they stand in or walk through the structure 605. UV-C lights 640 reside within the cavity 615 to disinfect air as it is pumped by the ejectors 250 and moved by the fan 625. Preferably, the UV-C lights 640 are in the form of UV-C LED strips, as shown at 342, and extend essentially from the back 614 to the front 612 of the structure.

Further variations of the air purification systems may fall within the spirit of the claims, below. The system may be utilized for the purpose of disinfecting moving vapor or fluid in a variety of industries and applications. It will be appreciated that the inventions are susceptible to modification, variation and change without departing from the spirit thereof.

I claim:

1. An air purification system for a passenger cabin of a transport vessel, comprising:
an elongated air compartment having a panel exposed to the passenger cabin, with a plurality of openings along the panel;
a plurality of ejector pumps placed along the air compartment, wherein each ejector pump comprises an air inlet side, an air outlet side to direct air into the air compartment, and a suction side that sealingly resides along a respective opening in the panel to draw air into the air compartment;
a plurality of air tubes, with each air tube having an inlet that receives a flow of compressed air, and an outlet connected to the air inlet side of a respective ejector pump;
at least one ultraviolet light (UV-C) emitting source residing at an inlet to the air compartment or within the air compartment, and configured to disinfect air moving through the air compartment; and
a plurality of air outlets placed along the panel, with each outlet configured to release air at selected points to provide a continuous distribution of filtered and disinfected air from the air compartment and into the passenger cabin.

2. The air purification system of claim 1, wherein:
the transport vessel is an airplane, a passenger train, a bus or a passenger ferry;
the air purification system further comprises a series of air filters residing at each of the plurality of openings; and
each of the plurality of ejector pumps resides internal to the elongated air compartment, and sealingly resides on a respective opening such that the suction side of each ejector pump draws air through a respective air filter of the series of air filters.

3. The air purification system of claim 2, wherein each of the plurality of air outlets comprises a nozzle.

4. The air purification system of claim 2, wherein each of the plurality of air outlets has a diameter no greater than 0.25 cm.

5. The air purification system of claim 2, wherein:
the plurality of air outlets comprises slots placed along the panel, with each slot being placed at an angle to minimize exposure of UV-C light to passengers in the passenger cabin;
the passenger cabin comprises a plurality of seats;
each of the plurality of air outlets comprises an adjustable gasper; and
each of the gaspers resides proximate one of the plurality of seats.

6. The air purification system of claim 3, wherein:
the passenger cabin comprises a plurality of seats;
each of the plurality of nozzles comprises an adjustable gasper; and
each of the gaspers resides above one of the plurality of seats.

7. The air purification system of claim 2, wherein the at least one ultraviolet light emitting source comprises a plurality of UV-C LED strips placed along the air compartment.

8. The air purification system of claim 2, wherein:
the air compartment serves as an air duct; and
the air duct is integrated into an air conditioning or ventilation system serving the passenger cabin.

9. The air purification system of claim 2, wherein the flow of air received at the inlet of each of the plurality of air tubes is compressed air taken from an existing source of compressed air of the transport vessel.

10. The air purification system of claim 2, further comprising:
at least one air circulation fan configured to move air along the air compartment; and
an air filter residing proximate an intake of the at least one fan.

15

11. The air purification system of claim 10, wherein:
the at least one ultraviolet light emitting source resides proximate an outlet of the at least one air circulation fan; and
the air purification system further comprises one or more internals exposed to the ultraviolet light, designed to interrupt the flow of air through the air compartment so as to enhance exposure of the air to the ultraviolet light.

12. The air purification system of claim 11, wherein each of the at least one air circulation fans pulls air from the passenger cabin or from an environment outside of the passenger cabin, and into an air duct before releasing the air into the air compartment.

13. The air purification system of claim 2, wherein the at least one ultraviolet light emitting source comprises a fluorescent UV light, an organic light-emitting diode ("OLED"), UV light emitting diodes, UV induction style lamps, or an electroluminescent lamp.

14. The air purification system of claim 2, wherein the air compartment is lined with a light-reflective material designed to increase a concentration of UV-C light generated by the at least one ultraviolet light-emitting source.

15. The air purification system of claim 2, wherein an interior of the air compartment comprises a coating of a photo catalyst material designed to reduce odor or volatile organic compounds within the passenger cabin.

16. The air purification system of claim 2, wherein the passenger cabin comprises a plurality of seats arranged in a plurality of rows, with an aisle reserved generally along a longitudinal axis of the passenger cabin, with seats placed along each side of the aisle forming port seats and starboard seats.

17. The air purification system of claim 16, wherein the elongated air compartment comprises a first air compartment residing over the port seats, and a second air compartment residing over the starboard seats.

18. The air purification system of claim 16, wherein the elongated air compartment resides above the aisle.

19. The air purification system of claim 2, wherein the air compartment comprises a plurality of modular sections, with each modular section having a panel that is hinged to an edge of the air compartment, and a latch configured to releasably secure the panel to the edge of the air compartment.

20. The air purification system of claim 19, wherein the air purification system further comprises one or more proximity sensors or switches configured to disable the ultraviolet light-emitting sources when a modular section of the panel is opened.

21. The air purification system of claim 2, wherein the air purification system further comprises at least one air manifold, with each of the at least one air manifold comprising an inlet that receives compressed air, and a plurality of air outlets, with each air outlet being in fluid communication with an inlet of a respective air tube such that the flow of air received at the inlet of each of the plurality of air tubes is delivered through the manifold.

22. The air purification system of claim 21, further comprising:
a plurality of internals placed along the length of the air compartment configured to redirect the flow of air through the air compartment so as to enhance exposure of the air to the ultraviolet (UV-C) light.

23. A portable air purification system, comprising:
a frame structure having an occupiable space;
an elongated air compartment supported by the frame structure above a ground surface, with the air compartment having an input end and a panel, and with a plurality of openings disposed along the panel;
one or more air filters residing along the panel at each of the plurality of openings;
one or more ejector pumps placed along the air compartment, wherein each ejector pump comprises an air inlet side, an air outlet side, and a suction side that sealingly resides above a respective opening in the panel to draw air into the at air compartment, through each of the one or more air filters;
one or more air tubes, with each air tube having an inlet that receives a flow of air, and an outlet connected to the air inlet side of a respective ejector pump of the one or more ejector pumps;
at least one ultraviolet (UV-C) light emitting source residing at the input end of the air compartment or within the air compartment, and configured to disinfect air moving through the air compartment; and
one or more air outlets also placed along the panel, with each air outlet configured to release a continuous distribution of filtered and disinfected air into the occupiable space within the frame structure.

24. The air purification system of claim 23, wherein each of the one or more air outlets has a diameter no greater than 0.25 cm.

25. The air purification system of claim 23, wherein:
the frame structure comprises horizontal support members, base frame members vertical support members, and an upper surface; and
the elongated air compartment runs along the upper surface of the frame structure.

26. The air purification system of claim 23, wherein:
the one or more air outlets comprises a plurality of air outlets; and
the plurality of air outlets comprises slots placed along the panel, with each slot being placed at an angle to minimize exposure of UV-C light to individuals within the frame structure.

27. The air purification system of claim 23, wherein:
the one or more air tubes comprises a plurality of air tubes; and
the flow of air received at the inlet of each of the plurality of air tubes comprises (i) compressed air taken from an air compressor, (ii) air generated by an air circulation fan, or (iii) both.

28. The air purification system of claim 23, further comprising:
an air intake filter placed at the input end of the air compartment; and
an air circulation fan also placed at the input end of the air compartment configured to move air through the air filter and into the air compartment.

29. The air purification system of claim 28, wherein:
the air intake filter comprises a high-efficiency particulate air (HEPA) filter residing proximate an intake of the air circulation fan; and
the at least one ultraviolet light emitting source comprises a fluorescent UV light, an organic light-emitting diode ("OLED"), UV-C LED strips, or an electroluminescent lamp.

30. The air purification system of claim 23, wherein the air compartment is lined with a light-reflective material designed to increase a concentration of UV-C light generated by the at least one ultraviolet light-emitting source.

31. The air purification system of claim 23, wherein the at least one ultraviolet light emitting source comprises a plurality of UV-C LED strips placed along the air compartment.

32. The air purification system of claim 23, wherein the frame structure further comprises tarps placed (i) along left and right sides of the tent structure, (ii) over the frame structure, providing a roof, or (iii) both.

33. The air purification system of claim 23, wherein the frame structure is placed within a building.

34. The air purification system of claim 23, wherein the frame structure resides along a sidewalk or a door entrance outdoors.

35. An air purification system, comprising:
- a compressed air source;
- an air purification chamber having a housing, wherein the housing comprises at least one air intake opening and a plurality of air release openings;
- at least one ejector pump having an air inlet, an air outlet, and a suction inlet, with the suction inlet of each of the at least one ejector pump being in fluid communication with a respective air intake opening of the housing;
- at least one air tube residing within the air purification chamber, wherein each of the at least one air tube comprises an inlet configured to receive compressed air from the compressed air source, and an outlet in fluid communication with a corresponding air inlet of an ejector pump;
- at least one internal residing within the air purification chamber arranged to disrupt a flow of air at the air outlet of the at least one ejector pump; and
- at least one ultraviolet (UV-C) light source residing along the air purification chamber configured to disinfect air flowing towards the air release openings in the housing.

* * * * *